US006770773B2

(12) United States Patent
Rose et al.

(10) Patent No.: US 6,770,773 B2
(45) Date of Patent: Aug. 3, 2004

(54) ORGANIC ACID-FE-OOH (FERROXANE) PARTICLES AND FERROXANE-DERIVED CERAMICS AND CERAMIC MEMBRANES

(75) Inventors: Jerome Rose, Rousset (FR); Mark Wiesner, Houston, TX (US); Andrew Barron, Houston, TX (US)

(73) Assignee: William Marsh Rice University, Houston, TX (US)

( * ) Notice: Subject to any disclaimer, the term of this patent is extended or adjusted under 35 U.S.C. 154(b) by 0 days.

(21) Appl. No.: 10/350,759

(22) Filed: Jan. 24, 2003

(65) Prior Publication Data

US 2003/0181320 A1 Sep. 25, 2003

Related U.S. Application Data

(60) Provisional application No. 60/351,448, filed on Jan. 24, 2002.

(51) Int. Cl.[7] ........................... C07F 15/02; B01J 31/00; C01G 49/02
(52) U.S. Cl. ...................... 556/138; 556/146; 501/126; 423/633; 423/634; 502/170; 502/172; 502/338; 502/438
(58) Field of Search ................................ 556/138, 146; 502/170, 172, 338, 438; 501/126; 423/633, 634

(56) References Cited

U.S. PATENT DOCUMENTS

| | | | |
|---|---|---|---|
| 3,346,422 A | * | 10/1967 | Berger .......................... 427/115 |
| 3,743,707 A | * | 7/1973 | Iwase et al. ................ 423/594.1 |
| 4,496,714 A | | 1/1985 | Murata et al. ................. 528/272 |
| 4,676,928 A | | 6/1987 | Leach et al. ................ 252/313.1 |
| 4,952,634 A | | 8/1990 | Grossman .................... 525/190 |
| 5,212,261 A | | 5/1993 | Stierman ...................... 525/806 |
| 5,240,472 A | | 8/1993 | Sircar ............................. 95/52 |
| 5,312,791 A | | 5/1994 | Coblenz et al. .............. 501/153 |
| 5,418,298 A | | 5/1995 | Laine et al. ................. 525/389 |
| 5,593,467 A | | 1/1997 | Monroe ........................ 51/309 |
| 5,593,781 A | | 1/1997 | Nass et al. .................... 428/403 |
| 6,024,890 A | * | 2/2000 | Poganiuch et al. ........ 252/62.58 |
| 6,206,942 B1 | | 3/2001 | Wood ........................... 51/309 |
| 6,207,130 B1 | | 3/2001 | Kareiva et al. .............. 423/600 |
| 6,369,183 B1 | | 4/2002 | Cook et al. ................... 528/10 |

FOREIGN PATENT DOCUMENTS

| | | |
|---|---|---|
| EP | 0 576 695 A1 | 1/1994 |
| WO | WO 97/23288 | 7/1997 |
| WO | WO 97/24297 | 7/1997 |

OTHER PUBLICATIONS

*Thermal Conductivity of Epoxy resin–Aluminium (0 to 50%); and Diavalent Chromium in Alkaline Earth Silicate Systems*; Chapman and Hall Ltd.; 1977; (pp. 1689–1691).

H. Schmidt et al., *Inorganic–Organic Hybrid Coatings for Metal and Glass Surfaces*, American Chemical Society 1995 (pp. 331–347).

(List continued on next page.)

*Primary Examiner*—Porfirio Nazario-Gonzalez
(74) *Attorney, Agent, or Firm*—Conley Rose, P.C.

(57) ABSTRACT

The present invention relates to ferroxanes and a method of making wherein a ferroxane may be defined by the general formula $[Fe(O)_x(OH)_y(O_2CR)_z]_n$ wherein x, y and z may be any integer or fraction such that $2x+y+z=3$ and n may be any integer. The ferroxanes may be doped with at least one other element other than iron. The present invention further relates to a ceramic made from the ferroxanes of the present invention and a method of making. The present invention still further relates to supported and unsupported membranes made from the ceramic of the present invention.

107 Claims, 6 Drawing Sheets

OTHER PUBLICATIONS

International Search Report for Application No. PCT/US 99/06137 dated Jul. 6, 1999 (4 p.).

Kareiva et al.; *Carboxylate–Substituted Alumoxanes as Processable Precursors to Transition Metal–Aluminum and Lanthanide–Aluminum Mixed–Metal Oxides: Atomic Scale Mixing via a New Transmetalation Reaction*; Chemistry of Materials, vol. 8, No. 9, 1996 (pp. 2331–2340).

Callender et al., *Aqueous Synthesis of Water–Soluble Alumoxanes: Environmentally Benign Precursors to Alumina and Aluminum–Based Ceramics*; Chemistry of Materials, vol. 9, No. 11, Nov. 1, 1997 (pp. 2418–2433).

Chemical Abstracts, vol. 111, No. 24, Dec. 11, 1989, abstract No. 218306m, UHLHORN, R.J.R.: High permselectivities of microporous silica modified gamma–alumina membranes: XP000181419.

Vogelson, Cullen T., et al., *Inorganic–Organic Epoxy Composite Materials Using Carboxylate–Alumoxanes*, Dept. of Chemistry, Rice University, Houston, TX, undated (11 pp.).

MacInnes, Andrew N., et al., *Indium tert–butylthiolates as single source precursors for indium sulfide thin films: is molecular design enough?*, Journal of Organometallic Chemistry, 449 (1993), p. 95–104.

H. Schmidt and H. Krug, "*Sol–gel–based inorganic–organic composite materials*", ACS Symp. Se. 572, No. Inorganic and Organometallic Polymers II, 183–194, (1994).

Y. Kimura, S. Tanimoto, H. Yamane, T. Kitao, "*Coordination Structure of the Aluminium Atoms of Poly (Methylaloxane), Poly (Isopropoxylaloxane) and Poly [Acyloxy Aloxane]*", Polyhedron, vol. 9, No. 2/3, 371–376, (1990).

Harry S. Katz, et al. *Handbook of Fillers and Reinforcements for Plastics*, Van Nostrand Reinhold Company, 1978 (49 p.).

Bryan Ellix, *Chemistry and Technology of Epoxy Resins*, Blackie Academic & Professional, an Imprint of Chapman & Hall, (80 p.).

R. Kasemann, H. Schmidt; *Coatings for Mechanical and Chemical Protection based on Organic–Inorganic Sol–Gel Nanocomposites*; New Journal of Chemistry, vol. 18, No. 10–1994; (pp. 1117–1123).

C. T. Vogelson, et al.; *Inorganic–Organic Hybrid and Composite Materials Using Carboxylate–Alumoxanes*; (undated) (pp. 8).

S. Pasynkiewicz, *Alumoxanes: Synthesis, Structures, Complexes and Reactions*, Polyhedron, vol. 9, No. 2/3, 1990 (25 p.).

K. Nakamae, et al; *Studies on Mechanical Properties of Polymer Composites by X–Ray diffraction: 3. Mechanism of Stress Transmission in Particulate Epoxy Composite by X–Ray Diffraction*; Polymer, 1992, vol. 33, No. 13; (pp. 2720–2724).

H. Jullien, et al. *The Microwave Reaction of Phenyl Glycidyl Ether with Aniline on Inorganic Supports: a Model for the Microwave Crosslinking of Epoxy Resins*; Polymer, vol. 37, No. 15; 1996; (pp. 3319–3330).

H. Schmidt, et al; *Chemistry and Applications of Inorganic–Organic Polymers*; Mat. Res. Soc. –Symp. Prac. vol. 73; 1986; (pp. 739–750).

J. deWit, et al; *Evaluation of Coatings—A Total System Approach*; Materials Science Forum, vol. 247 (1997) (pp. 69–82).

Jacqueline I. Kroschwitz, et al., *Encyclopedia of Polymer Science and Engineering*, vol. 6, *Emulsion Polymerization to Fibers, Manufacture*, A Wiley–Interscience Publication, 1985, (66 p.).

Christopher C. Landry, et al., *From Minerals to Materials: Synthesis of Alumoxanes from the Reaction of Boehmite with Carboxylic Acids*, Department of Chemistry, Harvard University, 1995 (11 p.)

A. Apblett, et al; *Synthesis and Characterization of Triethylsiloxy–Suybstituted Alumoxanes: Their Structural Relationship to the Minerals Boehmite and Diaspore*; American Chemical Society; 1992; (pp. 167–182).

Y. Koide, et al; $[Al_5(Bu)_5(\mu_3-O)_2((\mu-OH)_2(\mu-O_2CPh)_2]$: *A Model for the Interaction of Carboxylic Acids with Boehmite*; American Chemical Society 1995; (pp. 4026–4029).

Y. Koide, et al; *Alumoxanes as Cocatalysts in the Palladium–Catalyzed Copolymerization of Carbon Monoxide and Ethylene: Genesis of a Structure–Activity Relationship*; Organometallics, vol. 15, No. 9. (pp. 2213–2226).

A. MacInnes, et al; *Chemical Vapor Deposition of Gallium Sulfide: Phase Control by Molecular Design*; American Chemical society, 1993; (pp. 1344–1351).

R. S. Bauer, *Epoxy Resins*, American Chemical Society, 1985 (15 p.).

C. Landry, et al; *Siloxy–Substituted Alumoxanes: Synehesis from Polydialkylsiloxanes and Trimethylaluminium, and Application as Aluminosilicate Precursors*; J. Mater. Chem. 1993; (pp. 597–602).

K. Andrianov, et al; *Synthesis of New Polymers with Inorganic Chains of Molecules*; Journal of Polymer Science, vol. XXX, 1958 (pp. 513–524).

G. Whiteside, et al; Articles; *Molecular Self–Assembly and Nanochemistry: A chemical Strategy for the Synthesis of Nanostructures*; Science, vol. 254, Nov. 1991; (pp. 1312–1319).

Malcolm P. Stevens, *Polymer Chemistry, An Introduction*, Oxford University Press, 1990 (9 p.).

C. Vogelson, et al; *Inorganic–Organic Hybrid and Composite Material Using Carboxylate–Alumoxanes*; World Ceramics Congress, Jun. 14–19, 1998; (pp. 499–506).

J. M. G. Cowie, Professor of Chemistry, University of Stirling, *Polymers: Chemistry and Physics of Modern Materials*, Intertext Books, (13 p.).

Article entitled: "*Alumina gels that form porous transparent $Al_2O_3$*," Bulent E. Yoldas, Journal of Material Science 10, pp. 1856–1860, 1975.

Article entitled: "*The oxidation of ferrous hydroxide in chloride–containing aqueous media and pourbaix diagrams of greem rust one,*" Ph. Refait and J.–M.R. Génin, Corrosion Science, vol. 34, No. 5, pp. 797–819, 1993.

Article entitled: "*Alumina ultrafiltration membranes derived from carboxylate–alumoxane nanoparticles,*" C.D. Jones, et al., Journal of Membrane Science 193, pp. 175–184, 2001.

Article entitled: "*Synthesis and characterization of carboxylate–FeOOH nanoparticles (ferroxanes) and ferroxane–derived ceramics,*" Rose et al., Chem. Mater., vol. 14, pp. 621–628.

Article entitled: "*Characteristics of ultrafiltration ceramic membranes derived from alumoxane nanoparticles,*" Maria M. Cortalezzi et al., Journal of Membrane Science 205, pp. 33–43, 2002.

\* cited by examiner

X 2.000 μM/DIV
Z 150.000 nM/DIV

FIG. 4B

X 2.000 μM/DIV
Z 150.000 nM/DIV

ORGANIC ACID-FE-OOH (FERROXANE) PARTICLES AND FERROXANE-DERIVED CERAMICS AND CERAMIC MEMBRANES

CROSS-REFERENCE TO RELATED APPLICATIONS

This application claims the benefit of application 60/351,448 filed Jan. 24, 2002.

STATEMENT REGARDING FEDERALLY SPONSORED RESEARCH OR DEVELOPMENT

Not applicable.

FIELD OF THE INVENTION

The present invention relates to ferroxanes and a method of making wherein a ferroxane may be defined by the general formula $[Fe(O)_x(OH)_y(O_2CR)_z]_n$ wherein x, y and z may be any integer or fraction such that 2x+y+z=3 and n may be any integer. The ferroxanes may be doped with at least one other element other than iron. The present invention further relates to a ceramic made from the ferroxanes of the present invention and a method of making. The present invention still further relates to supported and unsupported membranes made from the ceramic of the present invention.

BACKGROUND OF THE INVENTION

Membrane mediated processes currently factor in solving many outstanding problems in engineering and technology including, but not limited to, water treatment, catalysis and fuel cells. Recent improvements in membrane materials and technology have collaborated to make membrane filtration economically competitive with traditional separation technologies for certain applications.

Inorganic membranes, because of a unique profile of characteristics, hold promise for application to specialized problems in science and engineering. Areas ripe for application of inorganic membranes include reduction of costs by capture of reusable by-products in the oil and petrochemical industry; improving efficiency of energy production from fossil fuels by cleaning the coal gasification process; removal of impurities and moisture from natural gas thereby improving the gas mining process; reducing waste in the pulp and papermaking process; and waste and water treatment.

Inorganic, e.g. ceramic or metallic, membranes have particular advantages over their organic counterparts. They are stable at high temperatures with ceramic membranes capable of operating at temperatures in excess of 1000° C. and tend to be resistant to degradation in the presence of reactive chemicals. Because of the wide variety of materials that may be used in the fabrication of inorganic membranes, resistance to corrosive liquids and gases, even at elevated temperatures, can be realized.

Typical methods of manufacture for inorganic and/or ceramic membranes include powder processing and the sol-gel method; see, for example, *Advances in Ceramics*, Vol. 9., Eds., J. A. Mangels and G. L. Messing, American Ceramic Society, Westville, Ohio, 1984 and B. E. Yoldas, *J. Mat. Sci.* 1975, vol. 10, p. 1856.

Powder processing features the use of environmentally toxic binders and solvents such as trichloroethylene in the synthesis of the powder. Moreover, synthesis of the powder is a bottom-top approach, whereby discrete colloidal aggregates and particles are likely built up from dissolved single molecules of precursor compounds., As a result, particle size tends to be difficult to control using the powder processing method, most likely due to difficulties in controlling the rate of polymerization for assembly to the aggregates. The resulting collection of aggregates usually possesses a broad distribution of particle sizes, that is, it is said to have a low polydispersity index (PDI). The resulting mixture may be pressed, extruded or slip cast to provide the so-called green body, a ceramic precursor in the form of a single mass requiring only subsequent high-temperature thermal treatment to provide the final ceramic product. Ceramics ultimately attained from such a mixture of colloidal particles possessing a low polydispersity index tend to have a similarly broad range of pore sizes. For example, it is typical using this method to obtain average pore sizes between about 5 $\mu$m (5,000 nm) and about 15 $\mu$m (15,000 nm) in average size; and porosity between about 30% and about 50% pore volume. Ceramic membranes often comprise separate layers, each layer having a characteristic pore size. Large-pore size layers impart mechanical strength and often serve as supports for smaller-pore size layers that serve as the filtration membrane. Small pore layers may be obtained by coating with particles of suitable dimension prepared by a sol-gel process comprising, steps of dispersion, gelation, drying and firing. Crucial to this process is the creation of a stable liquid dispersion, or sol, of the colloidal ceramic precursors. This may be achieved through the use of numerous solvents and additives including strong acids, plasticizers and binders. These toxic agents, combined with sec-butanol which is a common byproduct of the process, are all environmental liabilities of the sol-gel process. The sol-gel also suffers from the general liabilities encountered in any bottom-top approach as described above.

Thus, there remains a need within the art for inorganic ceramics and membranes that can be produced with minimal environmental impact. In particular, the problem of producing iron oxide-based ceramics and membranes without wasteful byproducts remains less than completely solved. Moreover, the problem of producing iron oxide based ceramics and membranes with good control over pore size while simultaneously offering mild processing conditions has heretofore not been adequately addressed within the art.

SUMMARY OF THE INVENTION

The present invention proposes the use of ferroxanes as an environmentally benign precursor to iron oxide ceramics. According to one embodiment of the process, the use of aqueous conditions in the method of making ferroxanes presents an environmentally agreeable alternative to processes utilizing organic solvents. Moreover, according to another embodiment, the method of making iron oxide ceramics from the ferroxanes of the present invention utilizes lower temperatures than those typically required in existing iron oxide ceramic processes. An added advantage of the method of making ferroxanes is a top-bottom approach wherein a bulk mineral is reacted with an organic species to form and stabilize small particles. According to one embodiment, the ferroxanes are particulate and exist as a highly monodisperse dispersion. As a result, according to another embodiment, iron oxide ceramics derived from the ferroxanes of the present invention are characterized by pores that tend to be uniform and very small.

The present invention discloses ferroxanes and a method of making wherein a ferroxane may be defined by the general formula $[Fe(O)_x(OH)_y(O_2CR)_z]_n$, wherein x, y and z may be any integer or fraction such that $2x+y+z=3$ and n may be any integer. The present invention further discloses a method of making ferroxanes that comprises reacting a mineral comprising iron with at least one organic acid.

The present invention further relates to a ceramic made from the ferroxanes of the present invention and a method of making wherein the ceramic comprises at least one oxide of iron and can be dense or porous with porosities ranging from about 5 vol % to about 80 vol % wherein the method comprises reacting a mineral comprising iron with at least one organic acid to form ferroxanes; and heat-treating the ferroxanes. The present invention still further relates to supported and unsupported membranes made from the ceramic of the present invention. In some embodiments, the ceramics may be doped to provide reactive ceramic membranes with catalytic properties with high utility in certain gaseous heterogeneous catalytic processes, e.g fuel cells, automotive catalysis and the like. Ferroxane-derived ceramics may also find utility in electrodes, capacitor components, electrical insulators and battery components.

DETAILED DESCRIPTION OF THE INVENTION

Figure 1:
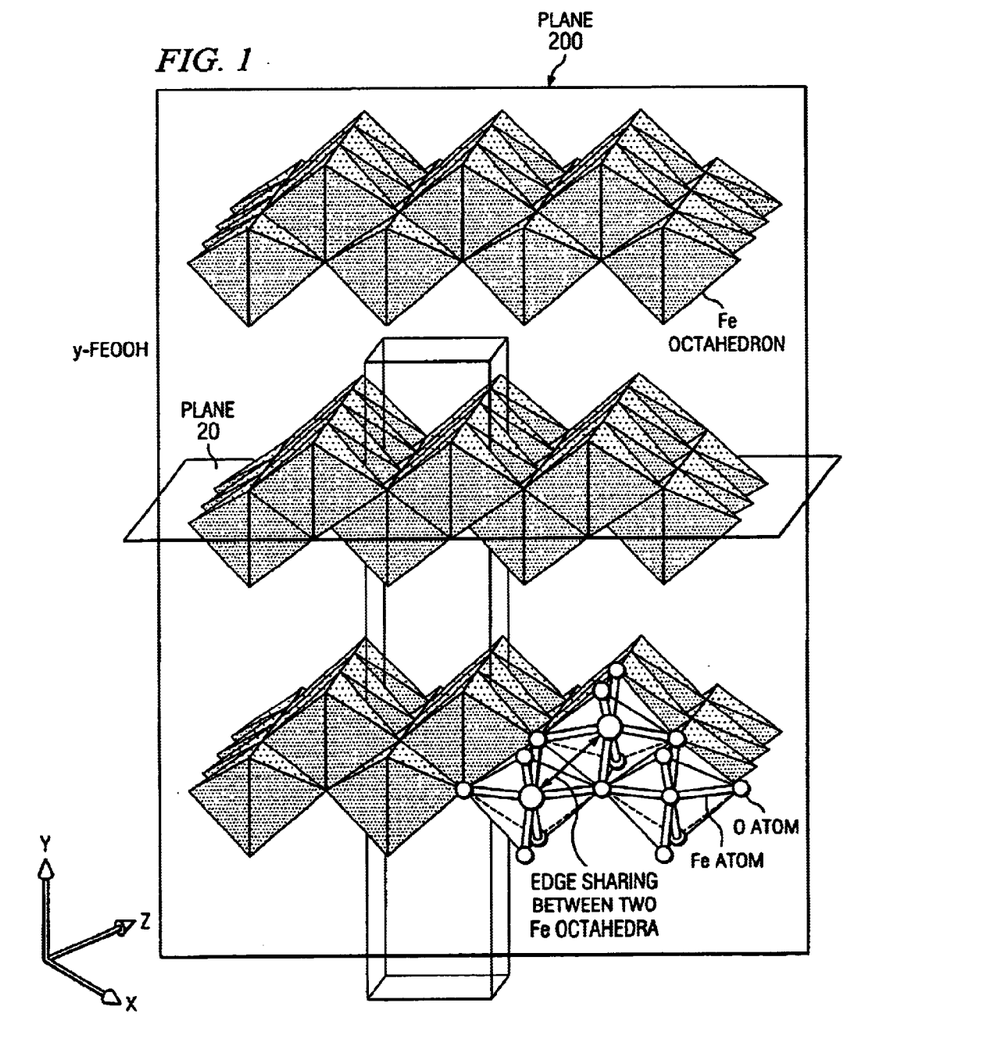
FIG. 1. Planes of Fe octahedra in $\gamma$-FeOOH shown to be bound by a network of hydrogen bonds in the 200 plane.

In one aspect, the present invention discloses a ferroxane of the general formula $[Fe(O)_x(OH)_y(O_2CR)_z]_n$, wherein x, y and z may be any integer or fraction such that $2x+y+z=3$ and n may be any integer. Though not wishing to be bound by any particular theory, one way to envision a ferroxane is to consider a γ-FeOOH crystal structure in which the layers of Fe octahedra are connected by hydrogen bonds along the 200 plane, as depicted in FIG. 1. In the case of ferroxanes from γ-FeOOH, one may further envision the hydrogen bonding positions being occupied by organic groups, such as carboxylate groups, that bond to adjacent octahedra within a layer of Fe octahedra. The layers of octahedra within the bulk material are thereby separated and dispersed into small particles of discrete size. Though not wishing to be bound to this scenario, it is thought that the conversion to ferroxanes is accompanied by a dramatic increase in the solubility of the dispersion over that of the bulk mineral owing to the presence of the carboxylate groups and connected alkyl chains.

The ferroxane of the present invention comprises at least one domain wherein the crystal lattice structure is consistent with FeOOH. FeOOH may exist in one of many different isomorphic crystal forms; for example, α, β, γ, and δ. Each form differs from the other based upon the precise arrangement of atoms within the crystal. This is typically revealed by XRD (X-ray diffraction) experiments. According to the present invention, the Fe of the ferroxane may be present in a crystal lattice structure consistent with any FeOOH isomorphic crystal form. However, preferred crystal forms include α-FeOOH, γ-FeOOH or the combination thereof. A particularly preferred crystal form according to the present invention is γ-FeOOH.

The ferroxane of the present invention further comprises carboxylate groups. According to the present invention, carboxylate groups are a suitable ligand for a mineral comprising iron. However, it shall be understood that any ligand that is suitably matched to the surface of the mineral of the present invention could also be effective. Some examples include, but are not limited to, phosphate and borate ligands. According to the present invention, the carboxylate groups are chemically bonded to the FeOOH crystal lattice in such a manner as to impart improved solubility of the ferroxanes. Preferably, the carboxylate groups are bonded to at least one Fe atom. More preferably, the carboxylate groups are bonded to at least two Fe atoms. Any carboxylate is suitable for use in the current invention; that is, any group derived from any suitable organic acid or ester. Preferably, the carboxylate is selected from the group consisting of acetate, methoxyacetate, ethoxyacetate, diethoxyacetate, aminoacetate and any combination thereof The ferroxane of the present invention may optionally be doped with at least one other element. As used herein "an element" and "a dopant" may be used interchangeably and will always mean something added to the ferroxane in any amount to change the physical and/or chemical characteristics of the ferroxane. Preferably, the element, i.e. the dopant, is present within the crystal lattice of the ferroxane. It shall be understood that within the crystal lattice can include inclusion within the interior of the crystal lattice or inclusion at one of the surfaces of the crystal lattice. It will be further understood that the dopant may be adsorbed onto the ferroxane crystal lattice or integrated into the structure of the ferroxane crystal lattice. Alternatively, the dopant atoms may be chelated by pendant groups, e.g. carboxylates, at the surface of the crystal lattice. According to the present invention, at least one element (the dopant) is present in an amount between about 0.0001% and about 50%. More preferably, at least one element is present in an amount between about 0.1% and about 10%. The dopant may be an element selected from the group consisting of the transition metals. As used herein, transition metals shall mean the metals in Groups IIIA, IVA, VA, VIA, VIIA, VIIIA, IB and IIB according to the Previous IUPAC Form of the Periodic Table of the Elements as found in, for example, the *CRC Handbook of Chemistry and Physics*, $82^{nd}$ Edition, 2001–2002, the reference to be used for all such element group numbers cited herein. However, a preferred group of elements that may be used as dopants in the present invention are selected from the group consisting of zirconium, cerium, manganese and molybdenum. Zirconium is a most preferred dopant for use in the present invention. According to one embodiment of the present invention, a dopant will be selected and added in a quantity sufficient to provide a ferroxane that is capable of accelerating the rate of at least one chemical process when present in said chemical process. In particular, according to this embodiment, the doped ferroxane shall act as a catalyst for at least one chemical process.

The ferroxanes of the present invention may exist in the form of soluble particles. Indeed, according to one non-binding theory, the ferroxanes of the present invention preferably exist in the form of small particles by virtue of the carboxylate groups that lie between the layers of FeOOH octahedra; the carboxylate groups thereby break up the bulk FeOOH mineral and provide for soluble, small ferroxane particles. Preferably, the particles are at least partially soluble in at least one solvent. More preferably, the ferroxanes particles are at least partially soluble in a solvent selected from the group consisting of water, tetrahydrofuran, methylene chloride, toluene, methanol and ethanol. Preferably, the ferroxane particles are soluble in at least one of the aforementioned solvents to the extent of at least 1 g/L.

Figure 3:
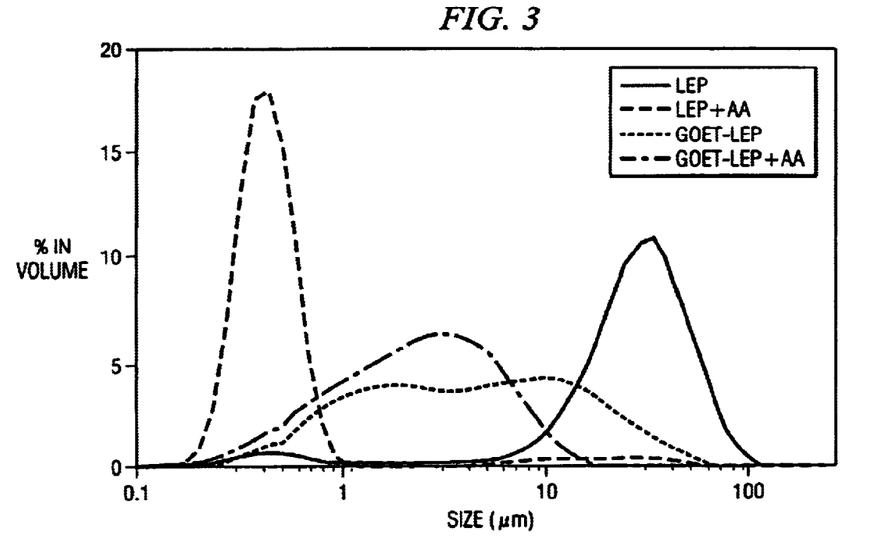
FIG. 3. Vol % of pores as a function of average particle size for FeOOH-acetic acid ferroxane.
Figure 5:
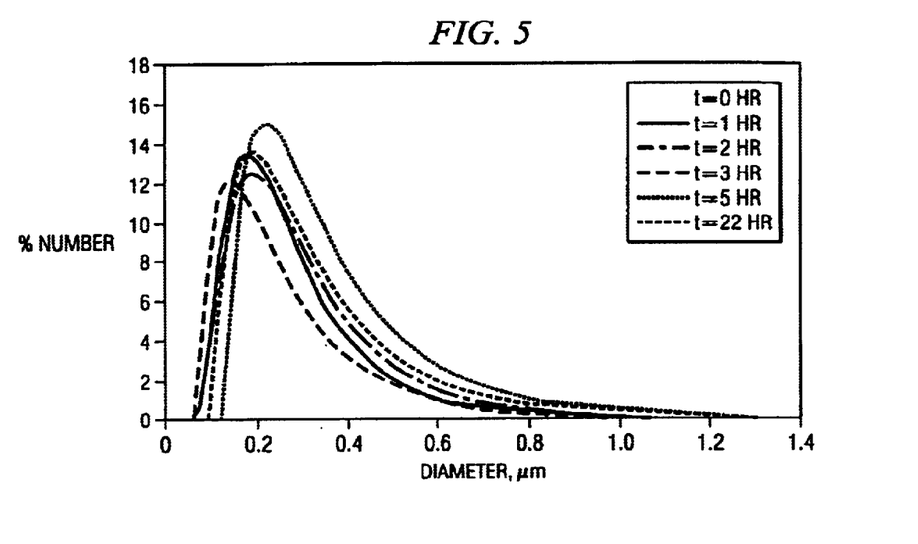
FIG. 5. Particle size distribution (number % vs. diameter, $\mu$m) for FeOOH-acetic acid ferroxane for various reaction times.
Figure 6:
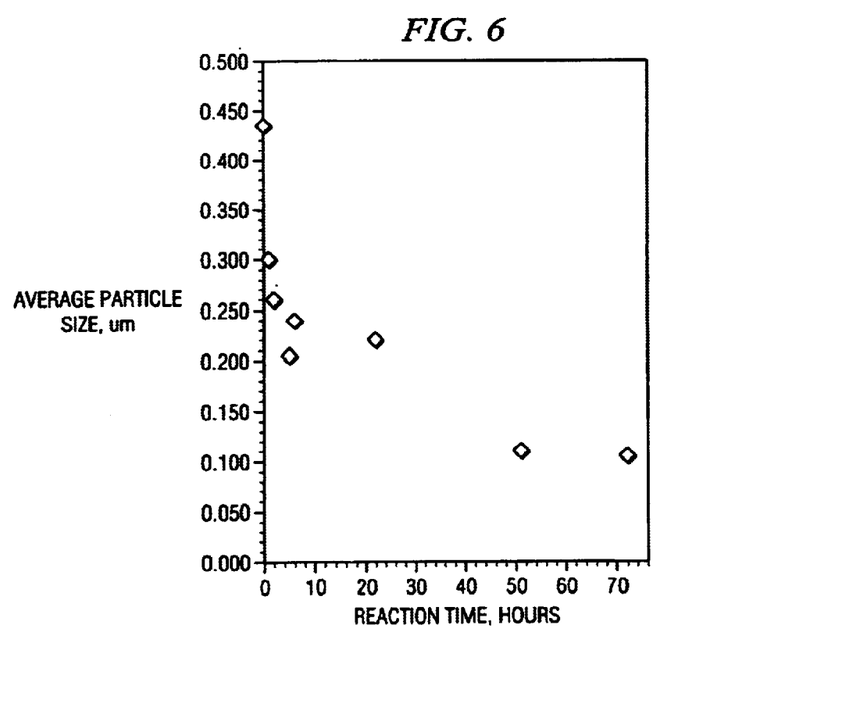
FIG. 6. Average particle size as a function of reaction time for FeOOH-acetic acid ferroxane.

According to one embodiment, the distribution of the particle sizes is highly monodisperse and small. As can be seen in FIG. 3, the FeOOH-acetic acid ferroxanes have a narrow particle size distribution, with most particles ranging in size between about 0.1 um and about 1 um. According to other embodiments of the process, the reaction conditions may be varied to provide particles of different sizes, as can be seen in FIG. 5 where longer reaction times tend to give narrower distributions. FIG. 6 demonstrates that up to a point, longer reaction times tend to give smaller average particle sizes. It is therefore not inconceivable that other conditions may exist which could give a wider range of distributions and sizes with respect to particle size. According to another embodiment, the average size of the particles is between about 0.005 $\mu$m and about 500 $\mu$m; preferably, between about 0.01 $\mu$m and about 50 $\mu$m; and more preferably, between about 0.1 $\mu$m and about 10 $\mu$m; and most preferably between about 0.1 $\mu$m and about 10 $\mu$m.

Figure 2:
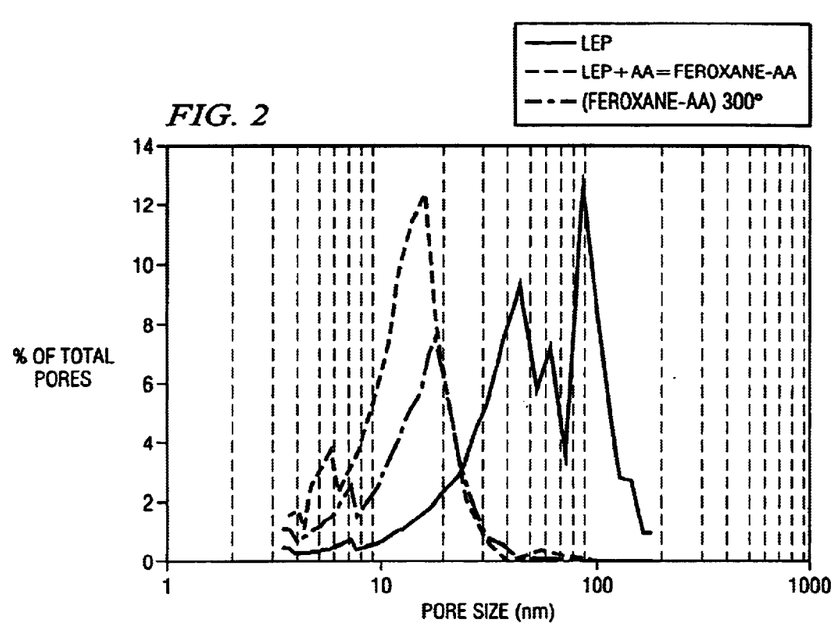
FIG. 2. Vol % of pores as a function of average pore diameter for FeOOH-acetic acid ferroxane before and after firing at 300° C.

The ferroxanes of the present invention have a certain profile of desirable physical characteristics. In particular, the ferroxanes possess characteristic morphology, porosity and pore size. As can be seen in FIG. 2, according to one embodiment, the distribution of pore sizes for FeOOH-acetic acid ferroxanes prior to heat-treatment at 300° C. is quite narrow, with an average pore size between about 10 nm and about 20 nm. The ferroxanes of the present invention may possess a surface area between about 25 $m^2$/g and about 500 $m^2$/g but will preferably possess a surface area between about 100 $m^2$/g and about 200 $m^2$/g; and an average pore diameter between about 2 nm and about 1000 nm; more preferably between about 2 nm and about 50 nm; and most preferably between about 5 nm and about 30 nm.

In another aspect, the present invention discloses a method of making a ferroxane comprising reacting a mineral comprising iron and at least one carboxylic acid under suitable conditions to provide a product mixture comprising at least some ferroxanes.

The present method comprises reacting a mineral comprising iron. Although there may be many minerals that comprise iron that could be used in the present invention, the minerals comprising iron that possess the formula FeOOH are particularly preferred.

FeOOH is found in many different isomorphic forms including those labelled as $\alpha$-, $\beta$-, $\gamma$- and $\delta$-FeOOH; the forms differing in the three-dimensional arrangement of the atoms within the crystal lattice. Preferably, the isomorphic form of FeOOH is selected from the group consisting of $\alpha$-, $\gamma$- and any combination thereof; but is most preferably $\gamma$-FeOOH.

The present method further comprises reacting a mineral comprising iron and at least one carboxylic acid. Although any suitable carboxylic acid could conceivably be used in the present invention, preferably, at least one carboxylic acid is selected from the group consisting of lysine, acetic acid, methoxyacetic acid, ethoxyacetic acid, diethoxyacetic acid and any combination thereof. More preferably, at least one carboxylic acid is acetic acid.

The present method still further comprises reacting a mineral comprising iron and at least one carboxylic acid under suitable conditions. Although one of normal skill in the art could envision many possible combinations of conditions that would be suitable for use in the present invention, preferred conditions comprise the use of 100% acetic acid. Suitable conditions still further comprise the use of an aqueous solvent; namely, water. Suitable conditions yet still further comprise a temperature of at least 70° C.; and still further comprise a period of time of at least 1 hour.

The present method may yet still further comprise isolating the ferroxanes from the product mixture. Preferably, isolating the ferroxanes comprises centrifuging the product mixture to provide a solid; and drying the solid where drying is preferably carried out under vacuum.

According to one embodiment of the present method, the method further comprises reacting a mineral comprising iron and at least one carboxylic acid under suitable conditions with at least one other element to provide a product mixture comprising at least some doped ferroxanes. The doped ferroxanes thus obtained are substantially similar those described hereinabove in connection with a previous aspect of this invention.

In one preferred embodiment of the present invention, conditions are suitable for providing a ferroxane in the form of particles. According to this embodiment, the average size of the particles is preferably between about 0.01 $\mu$m and about 500 $\mu$m.

The method of the present invention preferably produces porous ferroxanes having a high polydispersity index; that is, the sizes of the pores of the ferroxanes will have a very narrow distribtuion. In particular, the method is effective for creating a distribution of pore sizes in ferroxanes such that at least 75% of the pore volume is contained in pores between about 6 nm and about 40 nm. In another aspect of the invention, is disclosed a ceramic comprising at least one oxide of iron and possessing a a porosity between about 5 vol % and about 80 vol %. As used herein, a ceramic shall mean any porous inorganic material that is derived from the treatment of some inorganic mineral, salt, oxide or the like.

The ceramic of the present invention comprises an oxide of iron. Although many oxides of iron exist and the iron oxide of the ceramic is dependent upon the conditions used to make the ceramic, preferred oxides of iron include $\alpha$-$Fe_2O_3$, $\gamma$-$Fe_2O_3$, $Fe_3O_4$, $\alpha$-FeO or any combination thereof. A most preferred iron oxide is $\alpha$-$Fe_2O_3$, also known as hematite.

According to one embodiment, the ceramic of the present invention may further comprise at least one other element. This element may be known as a dopant and may be present anywhere within and/or on the iron oxide of the ceramic. By within, it shall be understood that the dopant may be part of the crystal lattice of the ceramic thereby forming a binary, ternary or other mixed metal oxide. Alternatively, the dopant may reside at surface sites of the ceramic to form a surface-modified ceramic. The element, or dopant, shall be present in the ceramic in an amount sufficient for modifying the chemical and/or physical properties of the ceramic. Preferably, between about 0.0001 wt % and about 50 wt % of the element is present in the ceramic. More preferably, between about 0.1 wt % and about 10 wt % of the element is present in the ceramic. The element may be selected from the group consisting of the transition metals. Preferably, the element is selected from the group consisting of zirconium, cerium, manganese and molybdenum. Most preferably, the element is zirconium. Also according to this embodiment, the ceramic is effective for accelerating the rate of at least one chemical process, that is the ceramic further comprising at least one other element may serve as a catalyst for at least one chemical process. The ceramic of the present invention is, by definition, a porous ceramic. Preferably, the average pore size is between about 10 nm and about 20 nm.

In yet another aspect of the present invention is presented a method of making a ceramic comprising reacting a mineral comprising iron and at least one carboxylic acid under suitable conditions to provide a product mixture comprising at least some ferroxanes; isolating the ferroxanes from the product mixture; optionally, reacting the ferroxanes with a compound comprising at least one other element under suitable conditions to provide a product mixture comprising at least some doped ferroxanes; and heat-treating the ferroxanes or doped ferroxanes in a manner sufficient for forming a ceramic.

The present method comprises reacting a mineral comprising iron and at least one carboxylic acid under suitable conditions to provide a product mixture comprising at least some ferroxanes. Although it is conceivable that there could be any one or combination of minerals comprising iron that could be used in the current invention, it is preferable that a mineral comprising iron is γ-FeOOH. Preferably, reacting a mineral comprising iron and at least one carboxylic acid is carried out under conditions suitable for providing particulate ferroxanes possessing an average size between about 50 $\mu$m and about 500 $\mu$m.

According to the present invention, a preferred method of making the γ-FeOOH of the present invention is via the oxidation of $FeCl_2$ in the presence of a base as described in Corrosion Science, 1993, vol. 34, pp. 797–819, incorporated herein by reference.

According to one embodiment, the present method may comprise reacting the ferroxanes with a compound comprising at least one other element under suitable conditions to provide a product mixture comprising at least some doped ferroxanes. It shall be understood that doped ferroxanes comprise at least one other element in addition to iron. Preferably, reacting the ferroxanes with a compound comprising at least one other element comprises heating a solution comprising the ferroxanes and a metal acetylacetonate at a temperature of at least 70° C. for a period of time of at least 1 hour. More particularly, the metal acetylacetonate is zirconium acetylacetonate. The element, or dopant, shall, as recited hereinabove, be added in an amount sufficient to effect some change in the chemical and/or physical properties of the ceramic. In particular, one compound comprising at least one other element is added in an amount sufficient to deliver between about 0.0001 wt % and about 50 wt % of the element to the ceramic. More preferably, at least one other element is added in an amount sufficient to deliver between about 0.1% and about 10% of the element to the doped ferroxanes. Preferably, the element is selected from the group consisting of the transition metals. More preferably, the element is selected from the group consisting of zirconium, cerium, manganese and molybdenum. Most preferably, the element is zirconium.

Figure 4A:
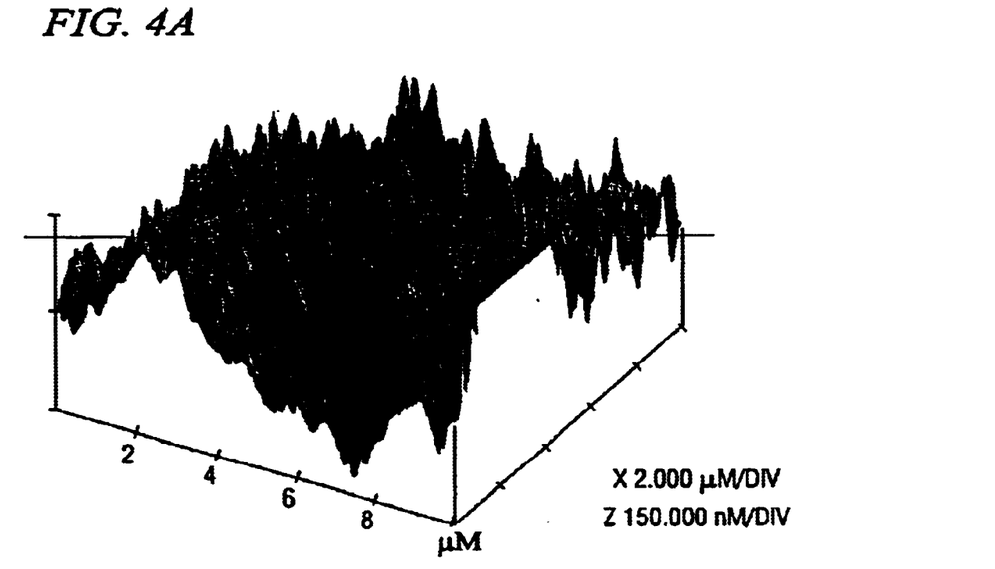
FIGS. 4A and 4B. Comparative atomic force microscopy (AFM) scans of FeOOH-acetic acid ferroxane before (4A) and after (4B) firing at 300° C.
Figure 4B:
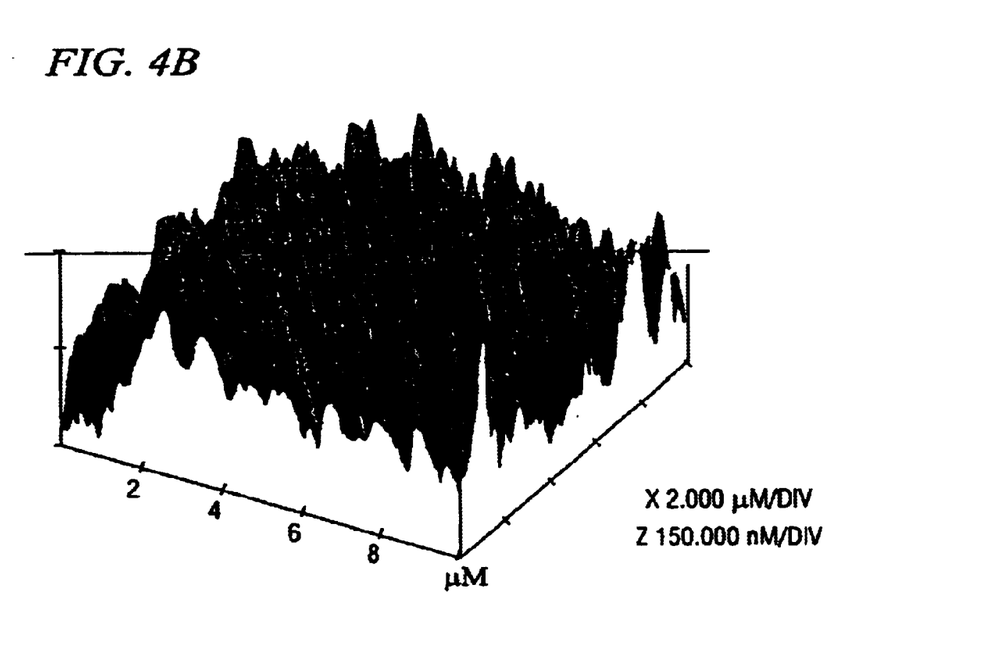

The present method further comprises heat-treating the ferroxanes or doped ferroxanes in a manner sufficient for forming a ceramic. It shall be understood that there are numerous conditions that may be effective for forming a ceramic. Ceramics may be formed from precursor particles. Ceramic manufacture typically involves subjecting a collection of such precursor particles to a set of conditions sufficient for fusing the particles into one porous mass. As can be seen in FIGS. 4A and 4B, wherein the surfaces of FeOOH-acetic acid ferroxane and FeOOH-acetic acid ferroxane-derived ceramic is shown via an atomic force microscope; although the roughness of the surface is obvious in both cases, a slight smoothing can be detected after sintering. Moreover, though not readily apparent from the Figure, maximum feature height is reduced from about 300 nm to less than about 200 nm. In the present invention, the conditions shall be those which can cause sintering and/or fusing of the ferroxanes or doped ferroxanes. In particular, heat-treating the ferroxanes or doped ferroxanes comprises exposing the ferroxanes or doped ferroxanes to a temperature between about 250° C. and about 500° C. More preferably, heat-treating the ferroxanes or doped ferroxanes comprises exposing the ferroxanes or doped ferroxanes to a temperature between about 250° C. and about 350° C.

The present method comprises heat-treating the ferroxanes or doped ferroxanes in a manner sufficient for forming a porous ceramic. According to one embodiment, heat-treating shall be carried out in a manner that is effective for providing a porous ceramic wherein 75% of the pore volume lies in pores of average diameter between about 10 nm and about 20 nm.

In yet another aspect of the current invention is disclosed a membrane comprising at least one oxide of iron wherein the membrane possesses pores of average diameter between about 5 nm and about 1000 nm; and a thickness between about 1 $\mu$m and about 1000 $\mu$m.

Figure 9:
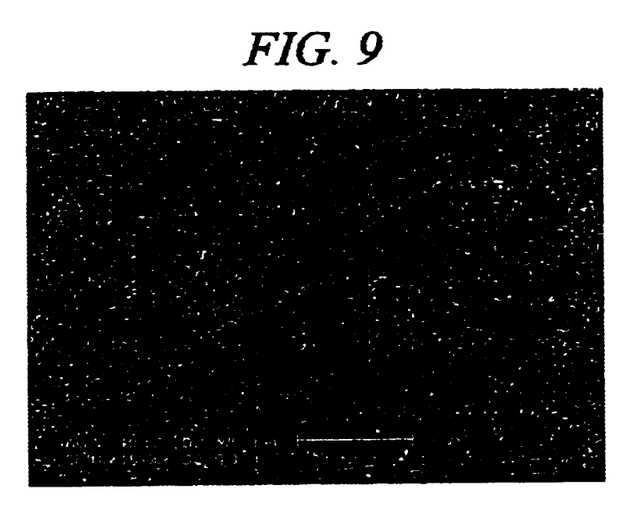
FIG. 9. Scanning electron microscope (SEM) image of the top surface of a FeOOH-acetic acid ferroxane-derived asymmetric membrane.
Figure 10:
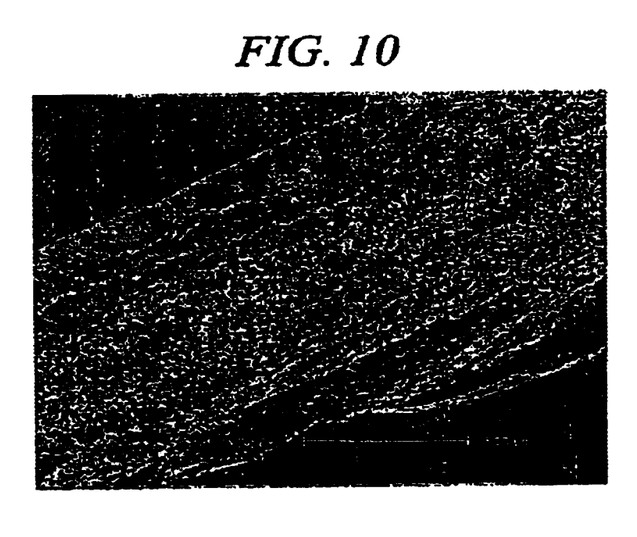
FIG. 10. SEM image of a cross section of a FeOOH-acetic acid ferroxane-derived asymmetric membrane comprising a glass fiber filter support.

According to one embodiment, the membrane may be supported. It shall be understood that a supported membrane is one that is supported on another porous layer of some material. A supported, or asymmetrical membrane, will typically comprise a least two porous layers. A thin, highly porous layer may lack mechanical stability and will typically require a porous support. Therefore, in an asymmetrical membrane, the thin highly porous layer is deposited onto a thicker layer with pores larger than that found in the thin, highly porous layer thereby imparting to the membrane the strength of the thick layer and the filtration properties of the thin layer. Also according to this embodiment, the membrane is preferably supported on a material selected from the group consisting of glass, ceramic and metal. FIG. 10 is a scanning electron microscope (SEM) image of a FeOOH-acetic acid ferroxane-derived ceramic asymmetric membrane in cross-section wherein the FeOOH-acetic acid ferroxane-derived layer can be viewed atop the glass fiber support. Similarly, FIG. 9 is a SEM image of a FeOOH-acetic acid ferroxane-derived membrane viewed from the top surface.

The present membrane comprises one oxide of iron. Although there exist many oxides of iron, $\alpha-Fe_2O_3$ is preferred.

According to one embodiment, the membrane may further comprise at least one other oxide of one other element. It shall be understood that such membranes comprising at least one other element in addition to iron may be referred to as doped membranes. The element, or dopant, may be selected from the group consisting of the transition metals; but is more preferably selected from the group consisting of zirconium, cerium, manganese and molybdenum; and is most preferably zirconium.

Figure 7:
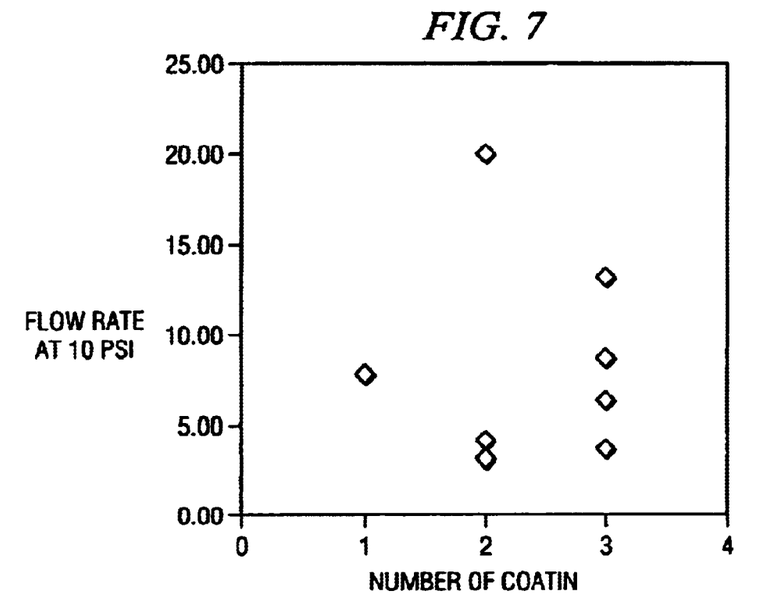
FIG. 7. Water flux at 10 psi though a FeOOH-acetic acid ferroxane-derived asymmetric membrane as a function of number of coats of ferroxane on the support.

The membrane of the present invention is particularly well-suited for use as an ultrafiltration membrane. Clean water flux measurements were conducted for membranes with one, two and three coating of ferroxanes. The measured flow rates are shown in FIG. 7. The variability in the results at each number of coatings is due to uneven coating of the supports, and thus, becomes more significant with increasing number of coatings. The lower permeability value obtained is taken as the correct one, meaning that almost all of the particles in the suspension were deposited onto the support evenly and completely convered its surface. Rejection data is shown in Table 1, below.

TABLE 1

REJECTION DATA FOR FERROXANE-DERIVED MEMBRANE

| Number of Coatings | Flow Rate (ml/min) | Flux ($m^3/m^2 * s$) | Resistance ($m^{-3}$) | Permeability |
|---|---|---|---|---|
| 1 | 8.71 | $9.02 \times 10^{-5}$ | $8.53 \times 10^{11}$ | $1.16 \times 10^{-12}$ |
| 2 | 4.50 | $4.66 \times 10^{-5}$ | $1.66 \times 10^{12}$ | $6.02 \times 10^{-13}$ |
| 3 | 3.93 | $4.07 \times 10^{-5}$ | $1.91 \times 10^{12}$ | $5.26 \times 10^{-13}$ |

Figure 8:
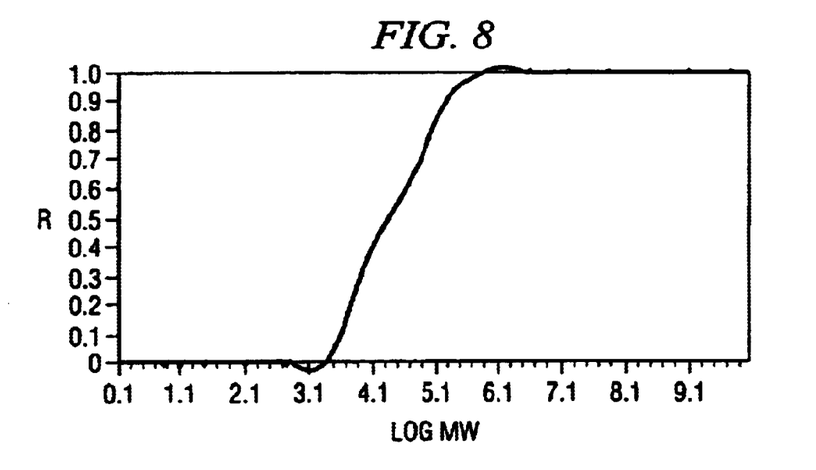
FIG. 8. Percentage of mass rejected as a function of molecular weight for a FeOOH-acetic acid ferroxane-derived asymmetric membrane.

According to one embodiment, the molecular weight cutoff measured by filtering a dextran solution was between 130,000 g/mol and 180,000 g/mol, with an average value of 150,000 g/mol. FIG. 8 shows a typical rejection curve of a ferroxane derived membrane. The sharpness of the cutoff is a consequence of the relatively narrow size distribution of the ferroxanes.

It is envisioned that the membrane of the present invention has many potential applications. It shall be apparent to one of normal skill in the art that there shall be many other applications of the present invention in addition to the applications explicity recited herein. The present membrane may be used as a water filtration membrane, for heavy metals adsorption, or gas filtration. It is also stable to acidic conditions making it particularly valuable for applications featuring corrosive environments or conditons.

In yet still a further aspect of the present invention is disclosed a method of making an unsupported ceramic membrane comprising reacting a mineral comprising iron and at least one carboxylic acid under suitable conditions to provide a product mixture comprising at least some ferroxanes; optionally, isolating the ferroxanes from the product mixture; optionally, reacting the ferroxanes with at least one compound comprising at least one other element to provide a product mixture comprising at least some doped ferroxanes; drying the ferroxanes or doped ferroxanes in a manner sufficient to provide a dry gel comprising ferroxanes or doped ferroxanes; and heat-treating the dry gel comprising ferroxanes or doped ferroxanes in a manner sufficient to provide an unsupported ceramic membrane.

The present method comprises reacting a mineral comprising iron and at least one carboxylic acid. Preferably, this is carried out in a manner effective for providing ferroxanes of average particle size between about 0.01 μm and about 10 μm.

The present method further comprises heat-treating the dry gel comprising ferroxanes or doped ferroxanes in a manner sufficient to provide an unsupported ceramic membrane. Conditions for heat-treating shall be sufficient for forming a porous ceramic from the dry gel comprising ferroxanes or doped ferroxanes. In particular, conditions will be sufficient for sintering and/or fusing the particles of the ferroxanes into a single, porous ceramic mass. Preferably, heat-treating the dry gel comprising ferroxanes or doped ferroxanes is carried out by subjecting the dry gel to a temperature between about 250° C. and about 350° C.

In another aspect, the invention discloses a method of making an asymmetric membrane comprising reacting a mineral comprising iron and at least one carboxylic acid under suitable conditions to provide a product mixture comprising at least some ferroxanes; optionally, isolating the ferroxanes from the product mixture; optionally, reacting the ferroxanes with at least one compound comprising at least one other element to provide a product mixture comprising at least some doped ferroxanes; depositing a suspension or solution of ferroxanes or doped ferroxanes onto a support; drying the suspension or solution of ferroxanes or doped ferroxanes in a manner sufficient to provide a dry gel comprising ferroxanes or doped ferroxanes on the support; and heat-treating the dry gel comprising ferroxanes or doped ferroxanes and the support in a manner sufficient to provide an asymmetric membrane comprising at least two porous layers.

The present method comprises depositing a suspension or solution of ferroxanes or doped ferroxanes onto a support. There are many suitable solvents which can be used in the present method including the common laboratory solvents such as ether, chloroform, methylene chloride, alcohols, ethyl acetate and the like. However, water is the preferred solvent for a suspension or solution of ferroxanes or doped ferroxanes. The supports used in the present method are substantially similar to those described above in connection with another aspect of this invention. In particular, a suspension or solution of ferroxanes or doped ferroxanes is deposited onto a support selected from the group consisting of glass fiber and ceramic.

EXAMPLES

The following examples are presented to illustrate the ease and versatility of the approach and are not to be construed as in any way limiting the scope of the invention.
Synthesis of FeOOH A NaOH solution was added to an aqueous solution of $FeCl_2.H_2O$ such that $[FeCl_2.H_2O]/[NaOH]=0.6$ and $[FeCl_2.H_2O]=0.06$ M to provide γ-FeOOH, as demonstrated in Refait, P.; Genin, J. -M. R. Corrosion Science, 1993, vol. 34, pp. 797–819.
Synthesis of Ferroxanes and Ceramic 2 g of γ-FeOOH and 100% acetic acid was added to water (50 mL) such that [Fe]/[acetic acid]=1.5 and brought to reflux at 80° C. overnight. The solution was centrifuged at 20000 rpm for 2 hours and volatiles were removed with vacuum ($10^{-2}$ Torr) at 90° C. Firing of the FeOOH-acetic acid ferroxanes at 300° C. gave the ceramic.
Doped Ferroxanes The FeOOH-acetic acid ferroxane was dissolved to prepare a 14 g/L solution in water and zirconium acetylacetonate ($[Zr]=1.5 \times 10^{-2}$ M) was added. The solution was brought to reflux at 80° C. overnight.

What is claimed is:

1. A ferroxane of the general formula $[Fe(O)_x(OH)_y(O_2CR)_z]_n$, wherein:
   x, y and z may be any integer or fraction such that 2x+y+z=3 and n may be any integer, wherein the ferroxane comprises at least one carboxylate group, and wherein the at least one carboxylate group is selected from the group consisting of acetate, methoxyacetate, ethoxyacetate, diethoxyacetate, aminoacetate and any combination thereof.

2. The ferroxane according to claim 1 wherein the ferroxane comprises at least one domain wherein the crystal lattice structure is consistent with γ-FeOOH.

3. The ferroxane according to claim 1 wherein the Fe of the ferroxane is present in a crystal lattice structure consistent with a FeOOH mineral.

4. The ferroxane according to claim 3 wherein the FeOOH is present as α-FeOOH, γ-FeOOH or the combination thereof.

5. The ferroxane according to claim 4 wherein the FeOOH is present as γ-FeOOH.

6. The ferroxane according to claim 1 wherein the at least one carboxylate group is bonded to at least one Fe atom.

7. The ferroxane according to claim 1 further comprising at least one other element.

8. The ferroxane according to claim 7 wherein the element is present within the crystal lattice of the ferroxane.

9. The ferroxane according to claim 7 wherein at least one element is present in an amount between about 0.0001% and about 50%.

10. The ferroxane according to claim 9 wherein at least one element is present in an amount between about 0.1% and about 10%.

11. The ferroxane according to claim 7 wherein at least one element is selected from the group consisting of the transition metals.

12. The ferroxane according to claim 11 wherein at least one element is selected from the group consisting of zirconium, cerium, manganes and molybdenum.

13. The ferroxane according to claim 12 wherein at least one element is zirconium.

14. The doped ferroxane according to claim 7 wherein the doped ferroxane is effective for accelerating the rate of at least one chemical process.

15. The ferroxane according to claim 1 wherein the ferroxane exists in the form of particles.

16. The ferroxane according to claim 15 wherein the ferroxane particles are at least partially soluble in at least one solvent.

17. The ferroxane according to claim 16 wherein the ferroxane particles are at least partially soluble in a solvent selected from the group consisting of water, tetrahydrofuran, methylene chloride, toluene, methanol and ethanol.

18. The ferroxane according to claim 17 wherein the ferroxane particles are soluble in at least one solvent to the extent of at least 1 g/L.

19. The ferroxane according to claim 15 wherein the average size of the particles is between about 0.005 $\mu$m and about 500 $\mu$m.

20. The ferroxane according to claim 15 wherein the average size of the particles is between about 0.01 $\mu$m and about 50 $\mu$m.

21. The ferroxane according to claim 15 wherein the average size of the particles is between about 0.1 $\mu$m and about 10 $\mu$m.

22. The ferroxane according to claim 15 wherein the average size of the particles is between about 0.1 $\mu$m and about 1 $\mu$m.

23. The ferroxane according to claim 1 wherein the surface area is between about 25 $m^2/g$ and about 500 $m^2/g$.

24. The ferroxane according to claim 1 wherein the surface area is between about 100 $m^2/g$ and about 200 $m^2/g$.

25. The ferroxane according to claim 1 wherein the average pore diameter is between about 2 nm and about 1000 nm.

26. The ferroxane according to claim 1 wherein the average pore diameter is between about 2 nm and about 50 nm.

27. The ferroxane according to claim 1 wherein the average pore diameter is between about 5 nm and about 30 nm.

28. The ferroxane according to claim 1 wherein the average pore diameter is between about 10 $\mu$m and about 20 $\mu$m.

29. The ferroxane according to claim 1 wherein the ferroxane is effective for accelerating the rate of at least one chemical process.

30. A method of making a ferroxane comprising:
reacting a mineral comprising iron and at least one organic acid under suitable conditions to provide a product mixture comprising at least some ferroxanes, wherein the ferroxanes comprise at least one carboxylate group.

31. The method according to claim 30 wherein a mineral comprising iron has the formula FeOOH.

32. The method according to claim 31 wherein the isomorphic form of FeOOH may be selected from the group consisting of α-, γ- and any combination thereof.

33. The method according to claim 32 wherein the isomorphic form of FeOOH is γ-FeOOH.

34. The method according to claim 30 wherein an organic acid is a carboxylic acid.

35. The method according to claim 34 wherein at least one carboxylic acid is selected from the group consisting of lysine, acetic acid, methoxyacetic acid, ethoxyacetic acid, diethoxyacetic acid and any combination thereof.

36. The method according to claim 35 wherein at least one carboxylic acid is acetic acid.

37. The method according to claim 30 wherein suitable conditions comprise reacting a mineral comprising iron with 100% acetic acid.

38. The method according to claim 30 wherein suitable conditions comprise reacting a mineral comprising iron and a carboxylic acid in an aqueous solvent comprising water.

39. The method according to claim 30 wherein suitable conditions comprise reacting a mineral comprising iron and a carboxylic acid at a temperature of at least 70° C.

40. The method according to claim 30 wherein suitable conditions comprise reacting a mineral comprising iron and a carboxylic acid for a period of time of at least 1 hour.

41. The method according to claim 30 further comprising:
isolating the ferroxanes from the product mixture.

42. The method according to claim 41 wherein isolating the ferroxanes comprises:
centrifuging the product mixture to provide a solid; and drying the solid.

43. The method according to claim 30 wherein the method comprises reacting a mineral comprising iron and at least one carboxylic acid under suitable conditions with at least one compound comprising at least one other element to provide a product mixture comprising at least some doped ferroxanes.

44. The method according to claim 43 wherein the compound comprising at least one other element is a metal acetylacetonate.

45. The method according to claim 43 wherein one compound comprising at least one other element is added in an amount sufficient to deliver between about 0.0001% and about 50% of the element to the doped ferroxanes.

46. The method according to claim 43 wherein one compound comprising at least one other element is added in an amount sufficient to deliver between about 0.1% and about 10% of the element to the doped ferroxanes.

47. The method according to claim 43 wherein one element is selected from the group consisting of the transition metals.

48. The method according to claim 47 wherein at least one element is selected from the group consisting of zirconium, cerium, manganese and molybdenum.

49. The method according to claim 48 wherein at least one element is zirconium.

50. The method according to claim 43 wherein the doped ferroxanes are effective for accelerating the rate of at least one chemical process.

51. The method according to claim 30 wherein the method is effective for providing a ferroxane in the form of particles.

52. The method according to claim 51 wherein the average size of the particles is between about 0.01 μm and about 500 μm.

53. The method according to claim 30 wherein the method is effective for creating a distribution of pore sizes in ferroxanes such that at least 75% of the pore volume is contained in pores between about 6 nm and about 40 nm.

54. Ferroxanes made according to the method of claim 30.

55. A ceramic comprising
at least one oxide of iron
and possessing a porosity between about 5 vol % and about 80 vol %, and wherein the average pore size is between about 10 nm and about 20 nm.

56. The ceramic according to claim 55 wherein the oxide of iron is selected from the group consisting of $\alpha$-$Fe_2O_3$, $\gamma$-$Fe_2O_3$, $Fe_3O_4$, $\alpha$-FeO and any combination thereof.

57. The ceramic according to claim 56 wherein the oxide of iron is $\alpha$-$Fe_2O_3$.

58. The ceramic according to claim 55 further comprising at least one other element.

59. The ceramic according to claim 58 wherein between about 0.0001 wt % and about 50 wt % of the element is present in the ceramic.

60. The ceramic according to claim 58 wherein between about 0.1 wt % and about 10 wt % of the element is present in the ceramic.

61. The ceramic according to claim 58 wherein one element is selected from the group consisting of the transition metals.

62. The ceramic according to claim 61 wherein at least one element is selected from the group consisting of zirconium, cerium, manganese and molybdenum.

63. The ceramic according to claim 62 wherein at least one element is zirconium.

64. The ceramic according to claim 63 wherein the ceramic is effective for accelerating the rate of at least one chemical process.

65. A method of making a ceramic comprising:
reacting a mineral comprising iron and at least one carboxylic acid under suitable conditions to provide a product mixture comprising at least some ferroxanes;
isolating the ferroxanes from the product mixture;
optionally, reacting the ferroxanes with a compound comprising at least one other element under suitable conditions to provide a product mixture comprising at least some doped ferroxanes; and
heat-treating the ferroxanes or doped ferroxanes in a manner sufficient for forming a porous ceramic.

66. The method according to claim 65 wherein a mineral comprising iron is $\gamma$-FeOOH.

67. The method according to claim 65 wherein reacting the ferroxanes with a compound comprising at least one other element comprises:
heating a solution comprising the ferroxanes and a metal acetylacetonate at a temperature of at least 70° C. for a period of time of at least 1 hour.

68. The method according to claim 65 wherein the compound comprising at least one other element is a metal acetylacetonate.

69. The method according to claim 68 wherein the metal acetylacetonate is zirconium acetylacetonate.

70. The method according to claim 65 wherein one compound comprising at least one other element is added in an amount sufficient to deliver between about 0.0001 wt % and about 50 wt % of the element to the ceramic.

71. The method according to claim 65 wherein one compound comprising at least one other element is added in an amount sufficient to deliver between about 0.1% and about 10% of the element to the doped ferroxanes.

72. The method according to claim 65 wherein one element is selected from the group consisting of the transition metals.

73. The method according to claim 72 wherein at least one element is selected from the group consisting of zirconium, cerium, manganese and molybdenum.

74. The method according to claim 73 wherein at least one element is zirconium.

75. The method according to claim 65 wherein heat-treating the ferroxanes or doped ferroxanes comprises exposing the ferroxanes or doped ferroxanes to a temperature between about 250° C. and about 500° C.

76. The method according to claim 65 wherein heat-treating the ferroxanes or doped ferroxanes comprises exposing the ferroxanes or doped ferroxanes to a temperature between about 250° C. and about 350° C.

77. The method according to claim 65 wherein heat-treating the ferroxanes or doped ferroxanes is carried out in a manner sufficient for providing a porous ceramic.

78. The method according to claim 77 wherein the porous ceramic possesses a pore size distribution wherein 75% of the pore volume lies in pores of average diameter between about 10 nm and about 20 nm.

79. The method according to claim 65 wherein reacting a mineral comprising iron and at least one carboxylic acid is carried out under conditions suitable for providing particulate ferroxanes possessing an average size between about 50 μm and about 500 μm.

80. A ceramic made according to the method of claim 65.

81. A membrane comprising:
at least one oxide of iron;
wherein the membrane possesses pores of average diameter between about 5 nm and about 1000 nm; and
a thickness between about 1 μm and about 1000 μm.

82. The membrane according to claim 81 wherein the membrane may be supported or unsupported.

83. The membrane according to claim 82 wherein the membrane is supported.

84. The membrane according to claim 83 wherein the membrane is supported on a material selected from the group consisting of glass, ceramic and metal.

85. The membrane according to claim 81 wherein one oxide of iron is $\alpha$-$Fe_2O_3$.

86. The membrane according to claim 81 wherein the membrane further comprises at least one other oxide of one other element.

87. The membrane according to claim 86 wherein one other element is selected from the group consisting of the transition metals.

88. The membrane according to claim 87 wherein one other element is selected from the group consisting of zirconium, cerium, manganese and molybdenum.

89. The membrane according to claim 88 wherein one other element is zirconium.

90. The membrane according to claim 81 wherein the membrane is a water filtration membrane.

91. The membrane according to claim 81 wherein the membrane is an ultrafiltration membrane.

92. The membrane according to claim 81 wherein the membrane has a molecular weight cutoff between about 100,000 g/mol and about 200,000 g/mol.

93. The membrane according to claim 91 wherein the the ultrafiltration membrane has a molecular weight cutoff between about 130,000 g/mol and about 180,000 g/mol.

94. The membrane according to claim 81 wherein the membrane is used for heavy metals adsorption.

95. The membrane according to claim 81 wherein the membrane is used for gas filtration.

96. The membrane according to claim 81 wherein the membrane is stable to acidic conditions.

97. A method of making an unsupported ceramic membrane comprising:

reacting a mineral comprising iron and at least one carboxylic acid under suitable conditions to provide a product mixture comprising at least some ferroxanes;

optionally, isolating the ferroxanes from the product mixture;

optionally, reacting the ferroxanes with at least one compound comprising at least one other element to provide a product mixture comprising at least some doped ferroxanes;

drying the ferroxanes or doped ferroxanes in a manner sufficient to provide a dry gel comprising ferroxanes or doped ferroxanes; and heat-treating the dry gel comprising ferroxanes or doped ferroxanes in a manner sufficient to provide an unsupported ceramic membrane.

98. The method according to claim 97 wherein reacting a mineral comprising iron and at least one carboxylic acid is carried out in a manner effective for providing ferroxanes of average particle size between about 0.01 μm and about 10 μm.

99. The method according to claim 97 wherein heat-treating the dry gel comprising ferroxanes or doped ferroxanes is carried out by subjecting the dry gel to a temperature between about 250° C. and about 350° C.

100. An unsupported ceramic membrane made according to the method of claim 97.

101. A method of making an asymmetric membrane comprising:

reacting a mineral comprising iron and at least one carboxylic acid under suitable conditions to provide a product mixture comprising at least some ferroxanes;

optionally, isolating the ferroxanes from the product mixture;

optionally, reacting the ferroxanes with at least one compound comprising at least one other element to provide a product mixture comprising at least some doped ferroxanes;

depositing a suspension or solution of ferroxanes or doped ferroxanes onto a support;

drying the suspension or solution of ferroxanes or doped ferroxanes in a manner sufficient to provide a dry gel comprising ferroxanes or doped ferroxanes on the support; and heat-treating the dry gel comprising ferroxanes or doped ferroxanes and the support in a manner sufficient to provide an asymmetric membrane comprising at least two porous layers.

102. The method according to claim 101 wherein the method is effective for providing in the asymmetric membrane, a surface area between about 110 $m^2$/g and about 150 $m^2$/g.

103. The method according to claim 101 wherein the method is effective for providing in the porous ferroxane-derived layer of the asymmetric membrane, an average pore diameter between about 10 nm and about 20 nm.

104. The method according to claim 101 wherein heat-treating comprises a temperature between about 250° C. and 500° C.

105. The method according to claim 101 wherein a suspension or solution of ferroxanes or doped ferroxanes is deposited onto a support selected from the group consisting of glass fiber, ceramic and the combination thereof.

106. The method according to claim 101 wherein water is used as the solvent for a suspension or solution of ferroxanes or doped ferroxanes.

107. An asymmetric membrane made according to the method of claim 101.

* * * * *